United States Patent
Niermann

(12)
(10) Patent No.: US 6,280,400 B1
(45) Date of Patent: Aug. 28, 2001

(54) DEVICE AND METHOD FOR SEPARATING COMPONENT OF A LIQUID SAMPLE

(75) Inventor: Volker Niermann, Little Falls, NJ (US)

(73) Assignee: Becton Dickinson and Company, Franklin Lakes, NJ (US)

(*) Notice: Subject to any disclaimer, the term of this patent is extended or adjusted under 35 U.S.C. 154(b) by 0 days.

(21) Appl. No.: 09/453,236

(22) Filed: Dec. 2, 1999

Related U.S. Application Data

(60) Provisional application No. 60/110,929, filed on Dec. 5, 1998.

(51) Int. Cl.[7] .................................................. D61B 5/00
(52) U.S. Cl. ............................................................. 600/573
(58) Field of Search ................................... 600/573, 577, 600/579

(56) References Cited

U.S. PATENT DOCUMENTS

| | | |
|---|---|---|
| 3,849,072 | 11/1974 | Ayres . |
| 4,083,788 * | 4/1978 | Ferrara .................. 210/516 |
| 4,088,582 | 5/1978 | Murty et al. . |
| 4,131,549 * | 12/1978 | Ferrara .................. 210/359 |
| 4,154,690 | 5/1979 | Ballies . |
| 4,257,886 | 3/1981 | Kessler . |
| 4,364,832 | 12/1982 | Ballies . |
| 4,417,981 * | 11/1983 | Nugent .................. 210/209 |
| 4,443,345 | 4/1984 | Wells . |
| 4,818,386 | 4/1989 | Burns . |
| 4,877,520 | 10/1989 | Burns . |
| 5,269,927 | 12/1993 | Fiehler . |
| 5,455,009 | 10/1995 | Vogler et al. . |
| 5,575,778 | 11/1996 | Hardt et al. . |
| 5,632,905 | 5/1997 | Haynes . |
| 6,063,297 * | 5/2000 | Antanavich et al. ......... 210/782 |

FOREIGN PATENT DOCUMENTS

| | | |
|---|---|---|
| 0 017 127 | 3/1980 | (EP) . |
| 0 627 261 A2 | 6/1994 | (EP) . |
| 0 638 804 A1 | 8/1994 | (EP) . |
| 6-222055 | 8/1994 | (JP) . |

* cited by examiner

Primary Examiner—Eric F. Winakur
Assistant Examiner—Pamela L. Wingood
(74) Attorney, Agent, or Firm—Nanette S. Thomas

(57) ABSTRACT

A vessel is disclosed that is useful for collecting a sample of a body fluid and, when subjected to centrifugation, separating the sample into a higher specific gravity phase and a lower specific gravity phase. The vessel of the invention includes an elongate tube that has an open end, a closed end and a sidewall. The sidewall has an outside surface and an inside surface and defines a receptacle with a central axis. The vessel has a closure disposed to fit the open end of the tube thereby sealing the receptacle. The vessel also includes an elongate separator releasably positioned at the open end of the tube that has a resilient top portion an elongate lower portion. The elongate lower portion has an axial passage therethrough. The top portion is sized to fit releaseably within the receptcle with an interference fit against the inside surface. When the vessel is subject to axial centrifugal force, the separator moves a distance axially from the open end toward the closed end.

3 Claims, 8 Drawing Sheets

DEVICE AND METHOD FOR SEPARATING COMPONENT OF A LIQUID SAMPLE

This application claims the benefit of Provisional No. 60/110,929 filed Dec. 5, 1998.

BACKGROUND OF THE INVENTION

1. Field of the Invention

This invention relates to a device and method for separating heavier and lighter fractions of a liquid sample. More particularly, this invention relates to a device and method for collecting and transporting liquid samples whereby the device and liquid sample are subjected to centrifugation in order to cause separation of the heavier fraction from the lighter fraction of the liquid sample.

2. Description of Related Art

Diagnostic tests may require separation of a patient's whole blood sample into components, such as serum or plasma, the lighter phase component, and red blood cells, the heavier phase component. Samples of whole blood are typically collected by venipuncture through a cannula or needle attached to a syringe or an evacuated collection tube. Separation of the blood into serum and red blood cells is then accomplished by rotation of the syringe or tube in a centrifuge. Such arrangements use a barrier for moving into an area adjacent the two phases of the sample being separated in order to maintain the components separated for subsequent examination of the individual components.

A variety of devices have been used in collection devices to divide the area between the heavier and lighter phases of a fluid sample.

The most widely used device includes thixotropic gel materials such as polyester gels. The present polyester gel serum separation tubes require special manufacturing equipment to prepare the gel and to fill the tubes. Moreover, the shelf-life of the product is limited in that overtime globules may be released from the gel mass. These globules have a specific gravity that is less than the separated serum and may float in the serum and may clog the measuring instruments, subsequently during the clinical examination of the sample collected in the tube.

Moreover, while the gel is chemically inert to blood samples, if certain drugs are present in the blood sample when it is taken, there can be an adverse chemical reaction with the gel interface.

Therefore, a need exists for a separator device that (i) is easily used to separate a blood sample; (ii) is non-temperature dependent during storage and shipping; (iii) is stable to radiation sterilization; (iv) employs the benefits of a thixotropic gel barrier yet avoids the many disadvantages of placing a gel in contact with the separated blood components; (v) minimizes red cell film or red cell hang-up of a blood sample; (vi) minimizes cross contamination of the heavier and lighter phases of the sample during centrifugation; (vii) minimizes adhesion of the lower and higher density materials against the separator device; (viii) is able to function in a plastic or glass container; and (ix) can be used with standard sampling equipment.

SUMMARY OF THE INVENTION

The present invention is a vessel useful for collecting a sample of a fluid and, when subjected to centrifugation, separating the sample into a higher specific gravity phase and a lower specific gravity phase. The vessel of the invention includes an elongate tube that has an open end, a closed end and a sidewall. The sidewall has an outside surface and an inside surface and defines a receptacle with a central axis.

The vessel has a closure disposed to fit the open end of the tube thereby sealing the receptacle. Alternatively, both ends of the tube may be open, and both ends of the tube may be sealed by elastomeric closures. At least one of the closures of the tube may include a resealable septum.

The vessel also includes an elongate separator releasably positioned at the open end of the tube that has a resilient top portion and an elongate lower portion. The elongate lower portion has an axial passage there through. The top portion is sized to fit releasably within the receptacle with an interference fit against the inside surface of the tube. When the vessel is subject to axial centrifugal force, the separator moves a distance axially from the open end toward the closed end.

The separator's position at the top of the receptacle and the separator's having a resilient top portion and a lower portion with a passage there through solves the problem of loading the sample into the tube between the separator and the bottom of the tube. The resilient top of the separator is easily penetrated by the sample delivery needle and thus the sample is delivered directly into the lower portion passage and the top surface of the separator is substantially not exposed to uncentrifuged sample. Then, when the vessel is centrifuged, the separator moves away from the open end of the tube and moves to a position between the lower and higher specific gravity phases of the sample. When the body fluid sample is blood, the higher specific gravity portions of the sample with the cellular components are between the separator and the bottom of the tube after centrifugation, and the cell free serum fraction is between the separator and the top of the tube. Since the separator moves axially down the tube inside surface during centrifugation and the sample is delivered into the tube below the separator, the interference fit between the separator top portion and the tube wall substantially eliminates the presence of red blood cells on the separator between the separator and the open end of the tube. The lower specific gravity serum phase of the sample is thus substantially free of cellular contamination.

DETAILED DESCRIPTION

Figure 1:
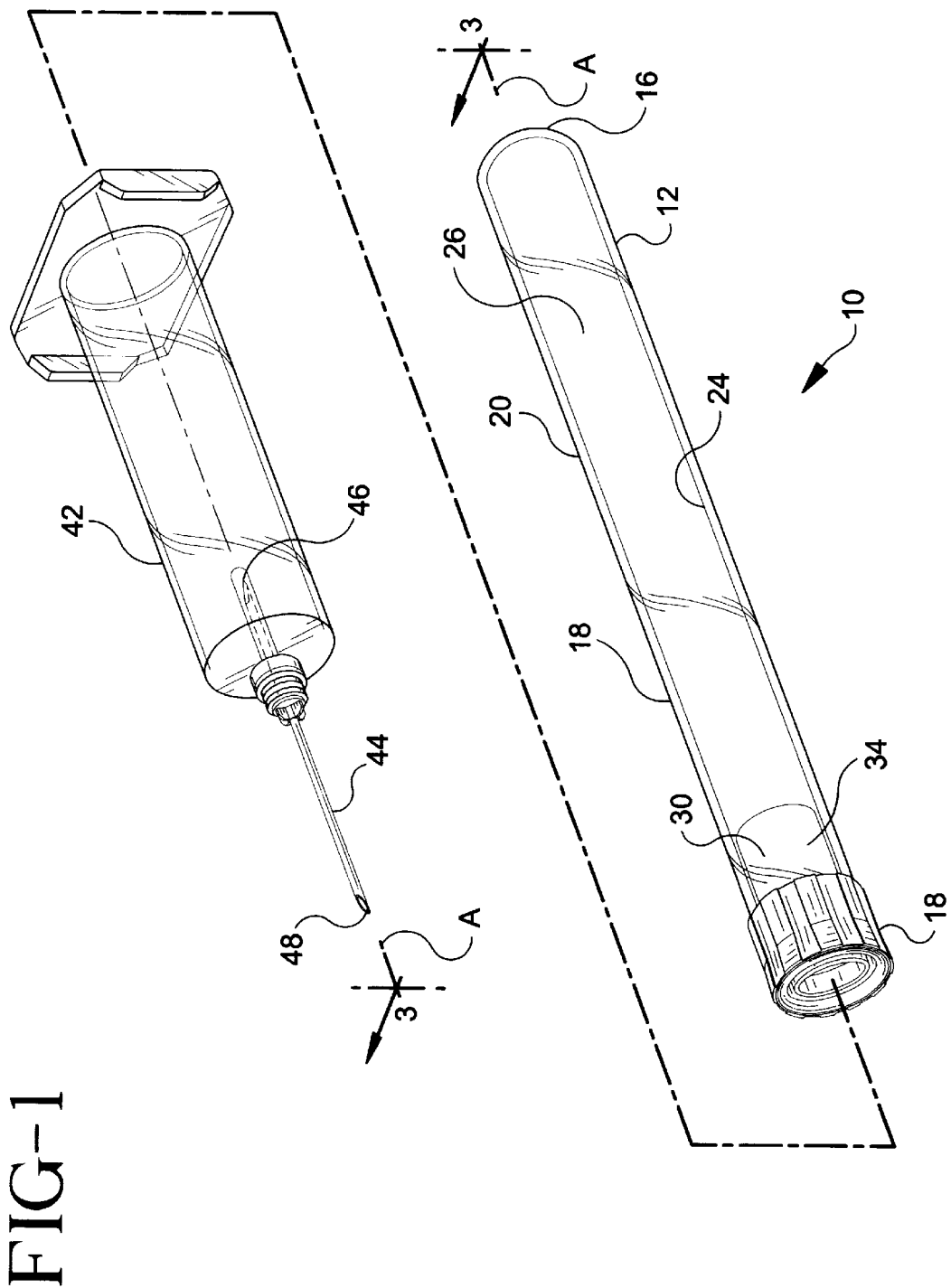
FIG. 1 is an exploded perspective view of the vessel of the invention with a needle holder.

While this invention is satisfied by embodiments in many different forms, there are shown in the drawings and herein described in detail, embodiments of the invention with the understanding that the present disclosure is to be considered as exemplary of the principles of the present invention and is not intended to limit the scope of the invention to the embodiments illustrated. The scope of the invention is measured by the appended claims and their equivalents. In this disclosure, the term "proximal" refers to the portions of the device closest to the practitioner and the term "distal" refers to the portion of the device away from the practitioner.

Referring to FIGS. 1–8, a vessel 10 of the present invention is useful for collecting a sample of a body fluid or other fluid samples and, when subjected to centrifugation, separating the sample into a higher specific gravity phase and a lower specific gravity phase. Vessel 10 of the invention includes an elongate tube 12 that has an open end 14, a closed end 16 and a sidewall 18. Sidewall 18 has an outside surface 20 and an inside surface 24 and defines a receptacle 26 with a central axis "A". Vessel 10 has a closure 18 disposed to fit over open end 14 of tube 12 and engage outside surface 20 of tube 12 thereby sealing receptacle 26. Vessel 10 also includes an elongate separator 30 releasably positioned at open end 14 of tube 12 that has a resilient top portion 32 and an elongate lower portion 34. Elongate lower portion 34 has an axial passage 36 there through. Top portion 32 is sized to fit releasably within receptacle 26 with an interference fit against inside surface 24. When vessel 10 is subject to centrifugal force, separator 30 moves a distance "x" axially from open end 14 toward closed end 16.

Figure 2:
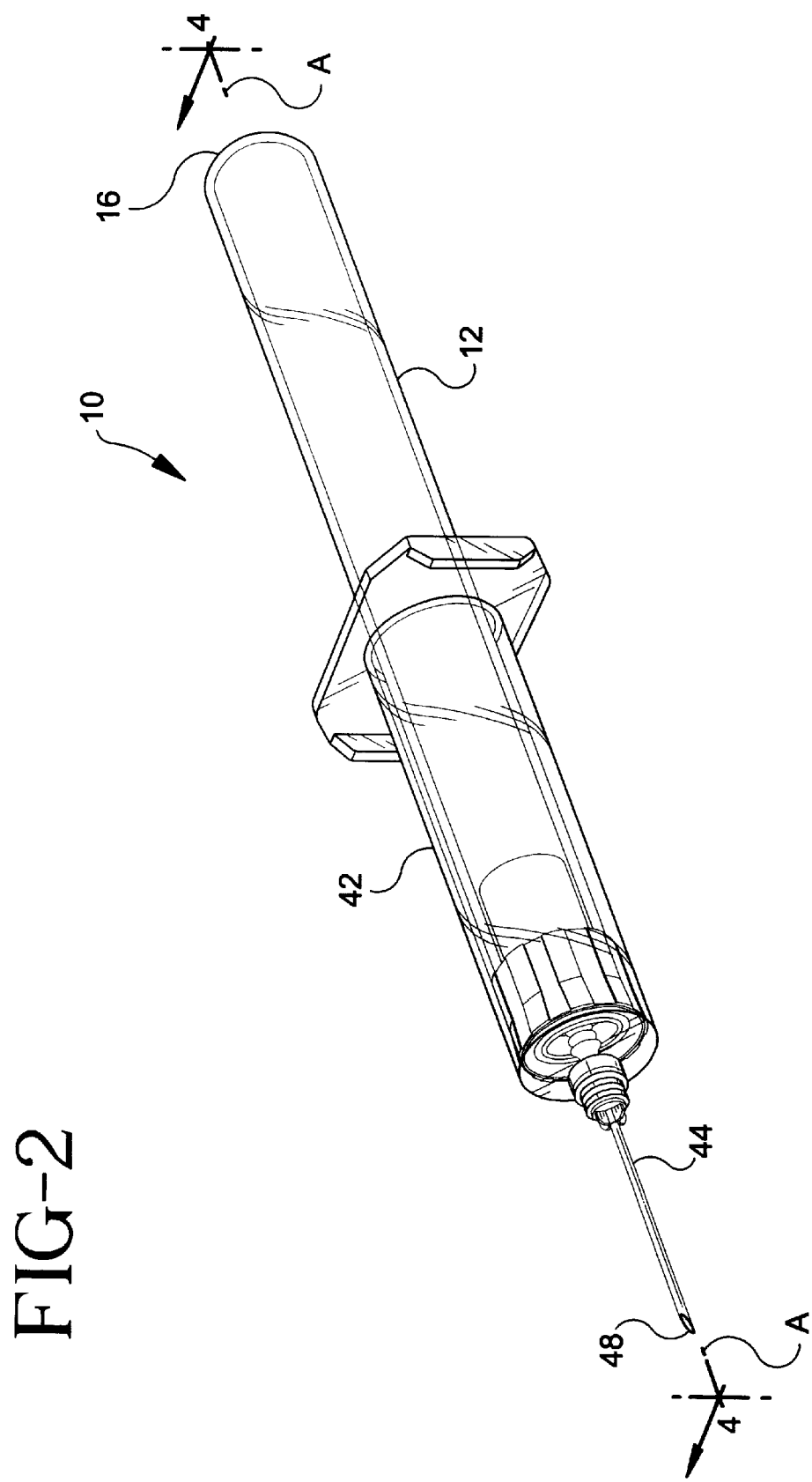
FIG. 2 is a perspective view of the vessel of the invention mounted in a needle holder.
Figure 3:
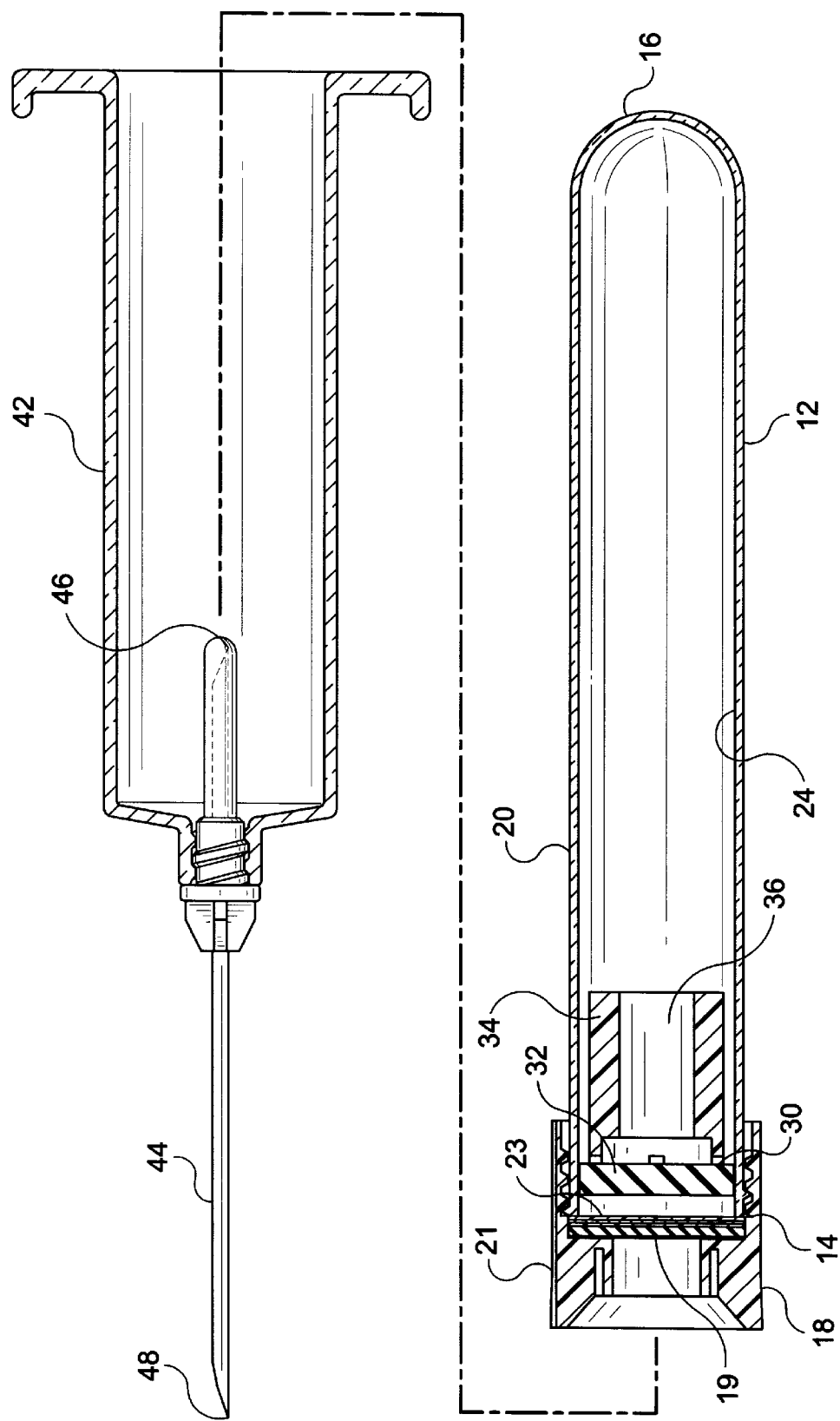
FIG. 3 is a longitudinal cross-sectional view of the vessel of the invention taken from FIG. 1 along the line 3—3.

FIGS. 1–3 illustrate the use of vessel 10 for collection of a blood sample 40 using a needle holder 42 with a hollow piercing element, illustrated as a double ended needle assembly 44 having a proximal end 46 and a distal end 48. In this usage, the placement of separator 30 within tube 12 at open end 14 positions the separator so that as proximal end 46 of needle assembly 44 penetrates closure 18, it also penetrates resilient top portion 32 of separator 30 delivering blood sample 40 into axial passage of elongate lower portion 34. Thus, blood sample 40 is introduced into receptacle 26 between closed end 16 and separator 30.

Figure 4:
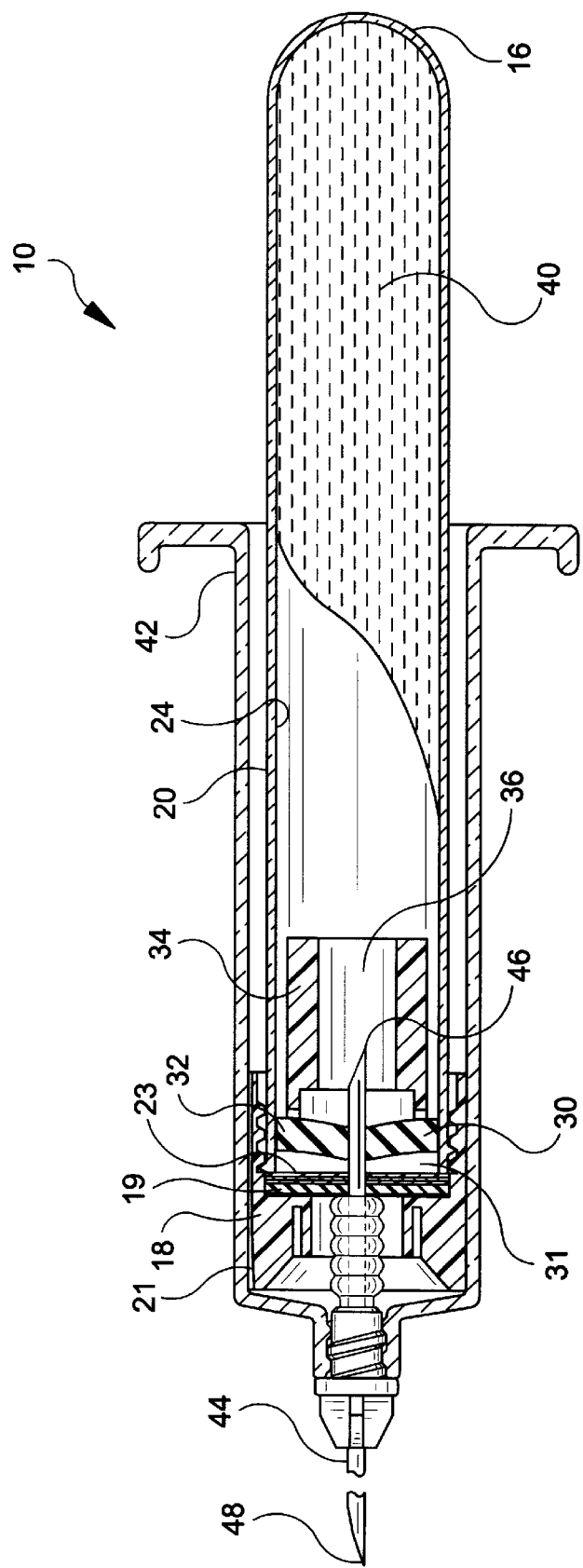
FIG. 4 is a longitudinal cross-sectional view of the vessel of the invention taken from FIG. 2, along the line 4–4 further illustrating the presence of a sample in the vessel.

Referring now to FIG. 4, this particular advantage of vessel 10 of the invention with separator 30 is illustrated. This demonstrates that top surface 31 of separator 30 is substantially free of any contact with blood sample 40.

Figure 5:
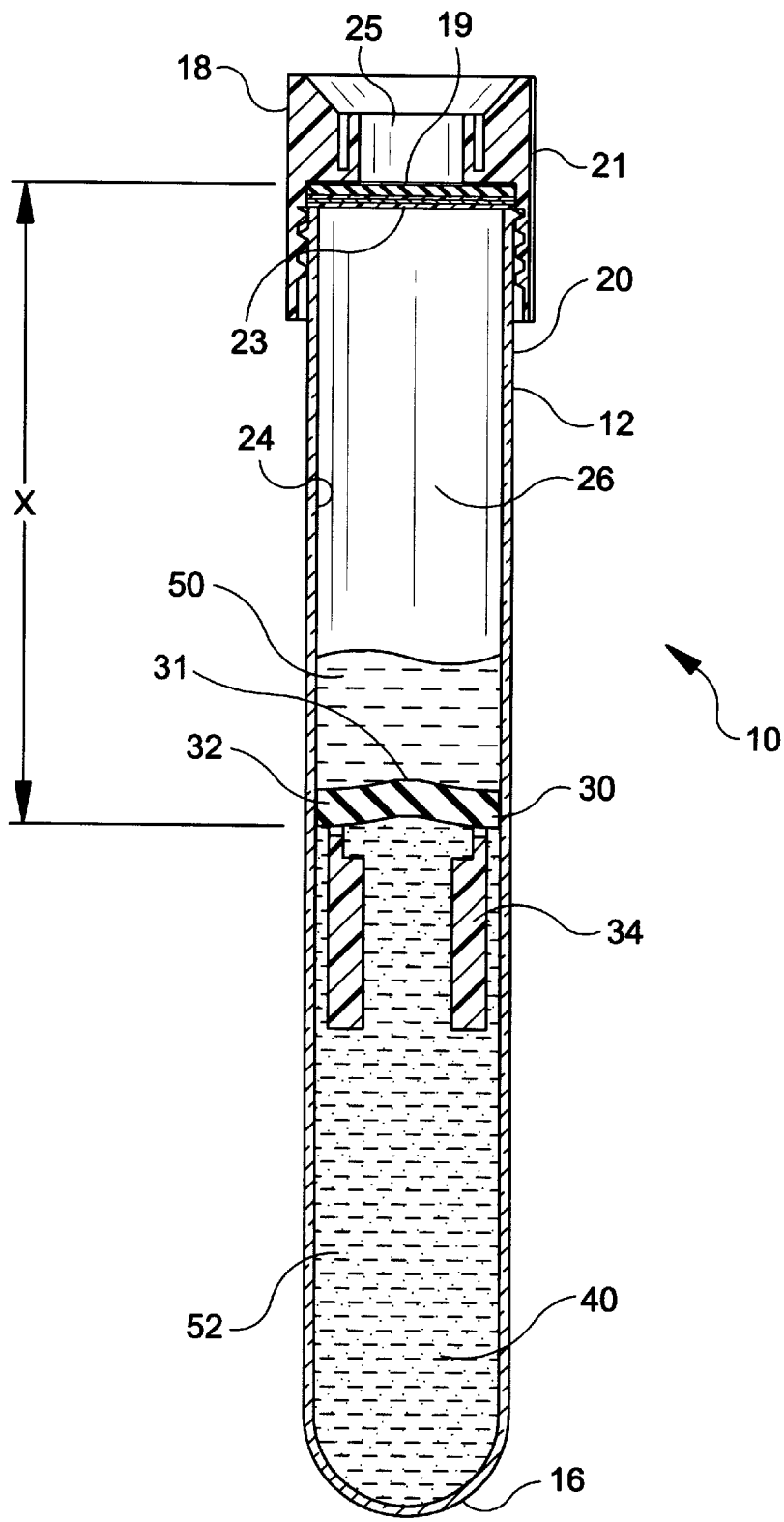
FIG. 5 is a cross-sectional view of the vessel of the invention with a sample therein during centrifugation.
Figure 6:
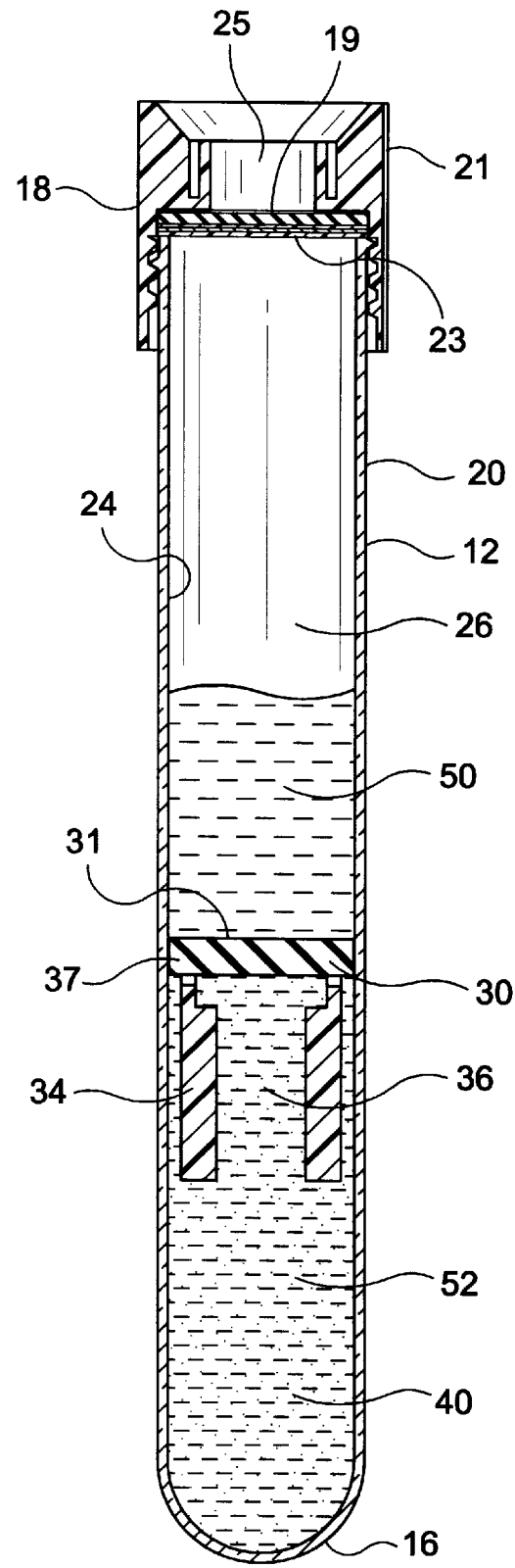
FIG. 6 is a cross-sectional view of the vessel of the invention with a separated ample therein after centrifugation.

When, vessel 10 is centrifuged as illustrated in FIGS. 5 and 6, separator 30, that preferably is formed from materials that provide the separator with a specific gravity between about 1.02 about 1.2, moves distance "x" under the influence of the centrifugal force toward closed end 16. As separator 30 descends toward closed end 16, a lower specific gravity fraction 50 of blood sample 40 moves between inside surface 24 of sidewall 18 and resilient top portion 32 by distorting the resilient top portion. As illustrated in FIGS. 5 and 6, during the centrifugation, as the separator descends, resilient top portion 32 exerts a wiping action on inside surface 24, and since top surface 31 of the separator has substantially not been exposed to blood sample 40, lower specific gravity phase 50 of the blood sample is substantially uncontaminated by any of the cellular materials found in a higher specific gravity fraction 52 of the blood sample.

As illustrated in FIG. 6, when the body fluid sample is blood and the specific gravity of separator 30 is in the preferred range of 1.03 to about 1.07, after centrifugation is completed separator 30 serves as a divider between lower specific gravity substantially cell free serum phase 50 and the higher specific gravity phase 52 including red blood cells and other higher density components.

Preferably, resilient top portion 32 is formed from a material that allows penetration by a piercing element such as needle assembly 44 and then recloses. Suitable materials for forming resilient top portion 32 include, are not limited to, polytetrafluorethylene foam, polyethylene foam, polyurethane foam and the like. Preferably, closed cell polyurethane and polyethylene foams such as are available from Sentinel Corp. are used. Suitable materials for forming elongate lower portion 34, include but are not limited to polytetrafluouroethylene, polyethyleneterephthalate and the like. Preferably, the material selected for forming elongate lower portion has a specific gravity greater than about 1.5. Preferably, lower portion 34 is formed from polyethyleneterephthalate.

Separator 30 may be formed from the materials selected by bonding resilient top portion 32 to the elongate lower portion 34 using adhesive bonding, solvent bonding, thermal bonding, ultrasonic bonding and the like. Alternatively, separator 30 may be formed in an injection molding process by co-injection of a resilient material to form top portion and a more rigid material to form elongate lower portion 34 in a single molding tool.

Preferably, tube 12 is formed from a substantially transparent and rigid material. Suitable materials for tube 12 include glass, polystyrene, polyethyleneterephthalate, polycarbonate and the like. Preferably, tube 12 is formed from polyethyleneterephthalate.

Vessel 10 of the invention is compatible with most of the numerous additives commonly used in sample collection tubes such as citrates, silicone, silicates, EDTA, and the like that are used to condition the sample either to facilitate or retard clotting, or to preserve the sample for a particular analysis. One or more of these additives may be utilized in the present invention for particular applications.

Vessel 10 preferably is evacuated to a preselected pressure below ambient atmospheric pressure to facilitate drawing a preselected sample volume. When vessel 10 is supplied with an internal pressure below ambient atmospheric pressure closure 18 should be formed from materials capable of maintaining the pressure differential during the expected shelf life of the vessel. Suitable materials for forming closure 18 include, but are not limited to natural rubber elastomer, synthetic thermoplastic and thermoset elastomeric materials such as Kraton, available from Shell and Santoprene, available from Monsanto. Additionally, composites of the elastomeric materials and gas barrier materials such as aluminized mylar and the like are also suitable for forming closure 18. Closure 18 may be in the form of a conventional resilient plug that fits within and occludes open end 14 of tube 12. Preferably, closure 18 includes a resilient elastomeric material in the form of a thin septum 19 that is held in position at open end 14 with a retention ring 21 that fits with an interference fit over outside surface 20 of tube 12. Preferably septum 19 has a gas barrier 23 that forms a reclosable seal around a penetrating element such as needle 44. Preferably retention ring 21 has an opening 25 there through to provide access to septum 19 by the needle assembly.

Figure 8:
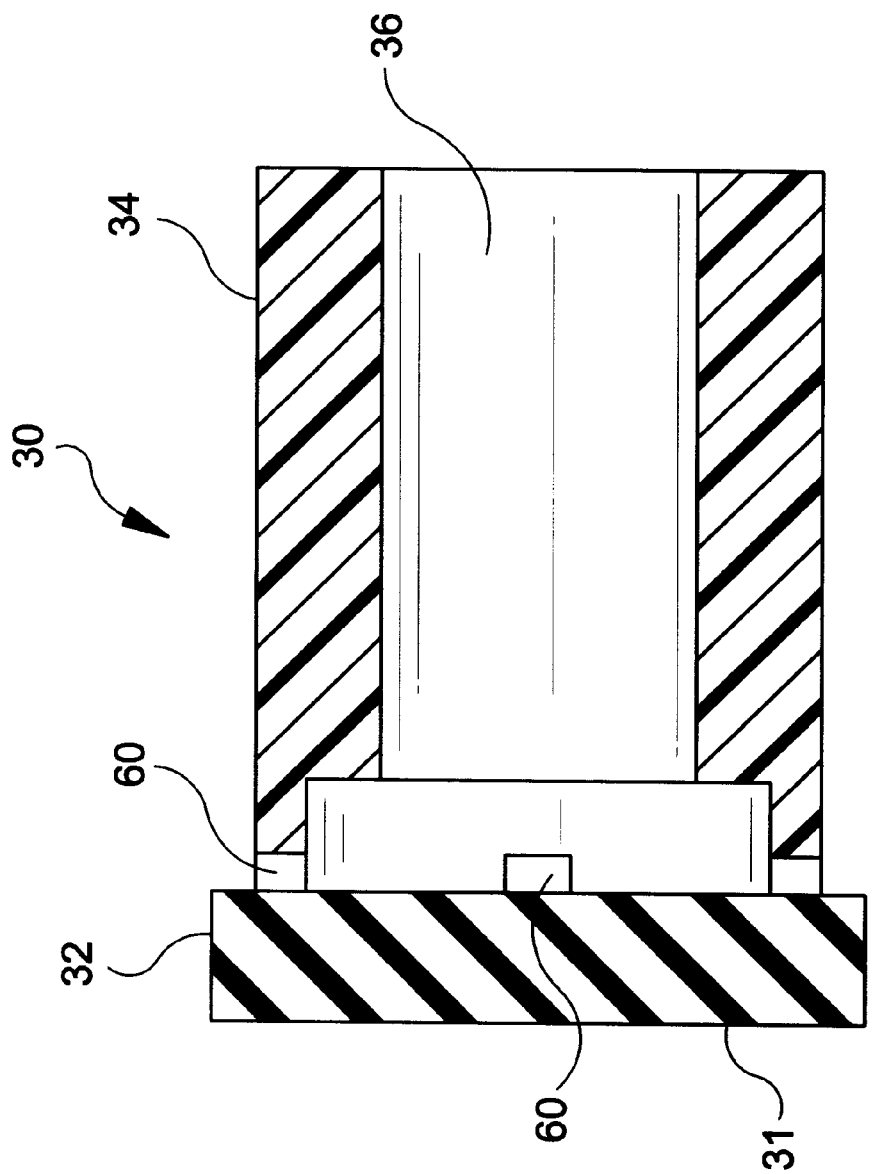
FIG. 8 is a longitudinal cross-section view of the separator element of the vessel of he invention taken from FIG. 7 along the line 8—8.

When closure assembly 18 is applied to tube 12, preferably the application is conducted in a chamber having a pressure reduced from ambient pressure. A preferred sequence for the manufacture of the invention is to place a plurality of tubes 12 into a rack system, meter a desired amount of additive or additives into the tube, then place separator 30 into open end 14 of the tube. Referring to FIG. 8, separator 30 preferably includes at least one air channel 60 to facilitate air flow from receptacle when separator 30 is placed in open end 14. Air channel 60 also facilitates upward movement of any gas or liquid trapped between separator 30 and the sample during centrifugation. Closure 18 is then loosely positioned on the tube and the racks, then the tubes are subjected to the preselected reduced pressure. While the tubes with the loosely positioned closures are under the reduced pressure, closure 18 is mechanically positioned over outside surface 20 to form a gas tight seal. The now completed vessel 10 is then ready for final processing, packaging and shipment.

Preferably, vessel 10 is supplied "sterile", this statement implies that vessel to has been exposed to conditions that would render any microorganism within receptacle 26 non-viable. Suitable conditions for rendering microorganisms non-viable include exposure to ionizing radiation, chemical sterilant agents and sufficient heat. Selection of materials for forming the components of vessel 10, and any additives should be made with consideration of the sterilization methods to be used to ensure that the materials selected are compatible with the sterilization conditions. Preferably, vessel 10 is exposed to ionizing radiation such as that produced by $Co^{60}$ or electron beam after labeling and in the final package for shipment.

Figure 7:
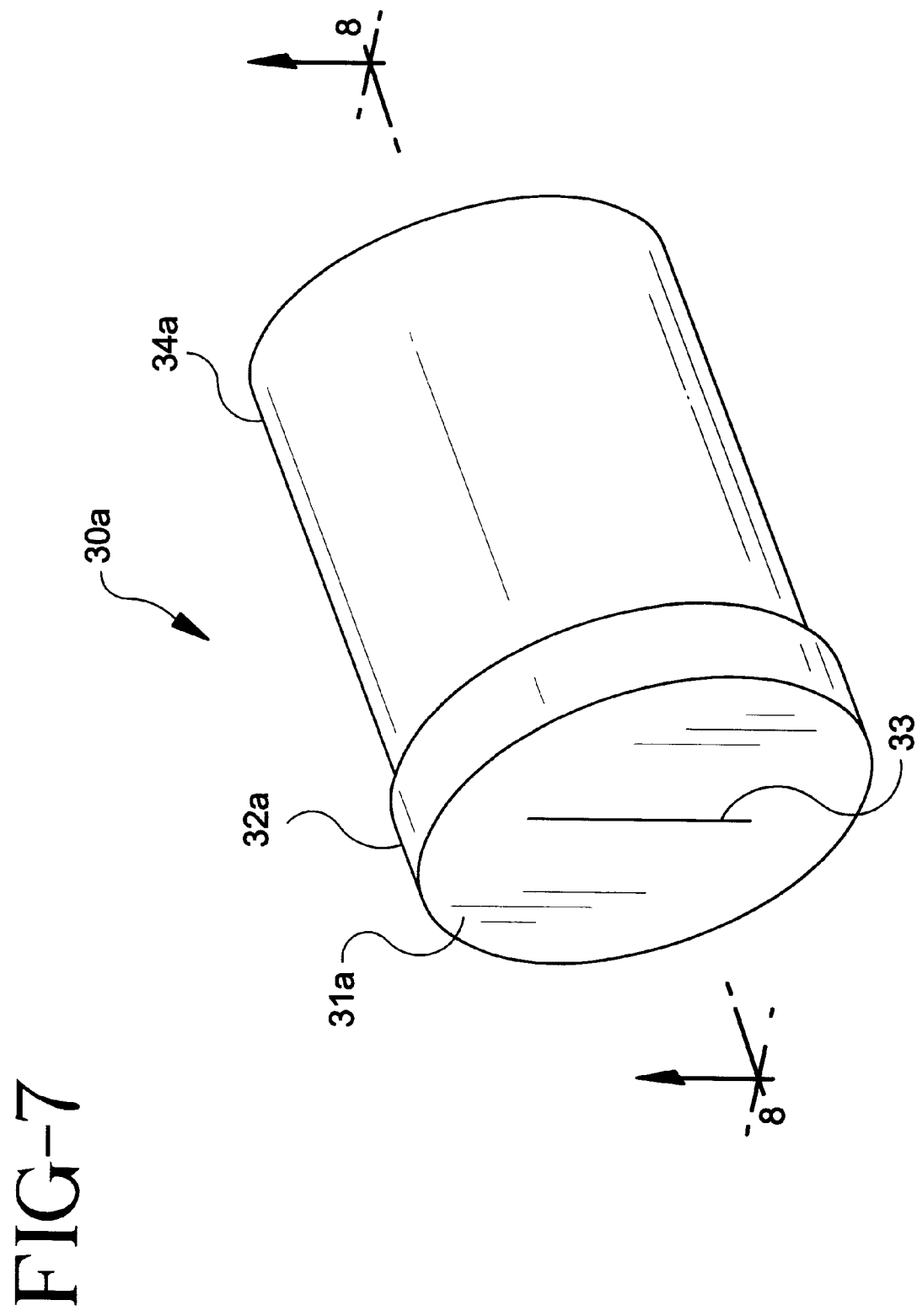
FIG. 7 is a perspective view of the separator element of the vessel of the invention.

Referring now to FIG. 7, a preferred embodiment of separator 30 is illustrated. In this embodiment, the structure of vessel 10 is substantially similar to the assembly illustrated in FIGS. 1–6. Accordingly, substantially similar components that perform substantially similar functions are numbered identically to those components of the embodiments of FIGS. 1–6, except that a suffix "a" is used to identify those components in FIG. 7. In this embodiment, separator 30a includes a resilient top portion 32a with a top surface 31a that includes a normally closed opening that preferably is a slit 33. Separator 30a further includes an elongate lower portion 34a with an axial passage 36a therethrough. In this embodiment, separator 30a is positioned in the open end of the tube and functions as illustrated in FIGS. 1–6. However, under the influence of centrifugal force, as separator 30a descends toward the closed bottom of the tube, slit 33 opens toward the open end of the tube and allows the lower density fraction to pass to top surface 31a between the open end of the tube and separator 30a. In addition to the illustrated slit 33, the opening may also be envisioned as a cross or other shapes for particular applications.

The vessel of the invention with separator 30 solves several problems. Separator 30 is releasably positioned at the open end of the tube so that the top surface of the separator substantially does not come into contact with untreated fluid samples. When the vessel used with a blood sample is centrifuged, only the substantially cell-free serum fraction of the sample is exposed to the top surface of the separator, thus providing practitioners with a clean sample. Additionally, the vessel of the invention does not require any additional steps or treatment by the practitioner. The sample is drawn in the standard fashion, using standard sampling equipment and centrifuged in the normal fashion. The art of providing substantially cell-free serum samples is advanced by the vessel of the invention.

What is claimed is:

1. A vessel useful for collecting a sample of a fluid and, when subjected to centrifugation, separating the sample into a higher specific gravity phase and a lower specific gravity phase comprising:

an elongate tube having an open end, a closed end and a side wall having an outside surface and inside surface defining a receptacle about a central axis;

a closure disposed to fit said open end of said tube thereby sealing said receptacle; and an elongate separator releaseably positioned at said open end of said tube, said separator having a resilient top portion and an elongate lower portion having an axial passage therethrough, said top portion being sized to fit said inside surface of said sidewall with an interference so that when said vessel is subjected to centrifugal force said separator moves a distance axially from said open end toward said closed end and comprising a normally closed opening therethrough aligned with said axial passage in said lower portion, wherein said normally closed opening comprises a slit in said resilient top portion of said separator, so that when said receptacle has the sample therein and said tube is subjected to the axial centrifugal force and said separater moves said distance from said open end toward said closed end, said slit opens and allows passage of said lower specific gravity phase of the sample to a position between said separater and said open end of said tube and said resilient top portion.

2. A vessel useful for collecting a sample of a fluid and, when subjected to centrifugation, separating the sample into a higher specific gravity phase and a lower specific gravity phase comprising:

an elongate tube having an open end, a closed end and a side wall having an outside surface and inside surface defining a receptacle about a central axis;

a closure disposed to fit said open end of said tube thereby sealing said receptacle; and an elongate separator releaseably positioned at said open end of said tube, said separator having a resilient top portion and an elongate lower portion having an axial passage therethrough, said top portion being sized to fit said inside surface of said sidewall with an interference so that when said vessel is subjected to centrifugal force said separator moves a distance axially from said open end toward said closed end, wherein said separator has a specific gravity between about 1.02 to about 1.2.

3. A vessel useful for collecting a sample of a fluid and, when subjected to centrifugation, separating the sample into a higher specific gravity phase and a lower specific gravity phase comprising:

an elongate tube having an open end, a closed end and a side wall having an outside surface and inside surface defining a receptacle about a central axis;

a closure disposed to fit said open end of said tube thereby sealing said receptacle; and an elongate separator releaseably positioned at said open end of said tube, said separator having a resilient top portion and an elongate lower portion having an axial passage therethrough, said top portion being sized to fit said inside surface of said sidewall with an interference so that when said vessel is subjected to centrifugal force said separator moves a distance axially from said open end toward said closed end, wherein said top portion of said separater is formed from a foam material selected from the group consisting of polyethylene foam and polyurethame foam.

* * * * *